US007341716B2

(12) United States Patent
Porter

(10) Patent No.: US 7,341,716 B2
(45) Date of Patent: Mar. 11, 2008

(54) OCCLUSIVE COMPOSITION

(75) Inventor: Stephen C. Porter, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1311 days.

(21) Appl. No.: 10/121,634

(22) Filed: Apr. 12, 2002

(65) Prior Publication Data

US 2003/0194389 A1 Oct. 16, 2003

(51) Int. Cl.
*A61K 31/785* (2006.01)
*A61F 13/00* (2006.01)
(52) U.S. Cl. .................................. 424/78.35; 424/422
(58) Field of Classification Search ................ 424/422, 424/78.35
See application file for complete search history.

(56) References Cited

U.S. PATENT DOCUMENTS

| | | | |
|---|---|---|---|
| 2,721,858 A | 10/1955 | Joyner et al. | |
| 3,142,698 A | 7/1964 | Halpern et al. | |
| 3,254,111 A | 5/1966 | Hawkings et al. | |
| 3,355,482 A | 11/1967 | Coover, Jr. et al. | |
| 3,463,804 A | 8/1969 | Ray et al. | |
| 3,654,340 A | 4/1972 | Banitt | |
| 3,701,771 A | 10/1972 | Almen et al. | |
| 3,940,362 A | 2/1976 | Overhults | |
| 3,975,422 A | 8/1976 | Buck | |
| 4,012,402 A | 3/1977 | Buck | |
| 4,364,921 A | 12/1982 | Speck et al. | |
| 4,847,065 A | 7/1989 | Akimova et al. | |
| 5,140,084 A | 8/1992 | Mikuni et al. | |
| 5,202,352 A | 4/1993 | Okada et al. | |
| 5,359,101 A | 10/1994 | Woods et al. | |
| 5,504,252 A | 4/1996 | Klemarczyk | |
| 5,624,669 A | 4/1997 | Leung et al. | |
| 5,695,480 A | 12/1997 | Evans et al. | |
| 5,702,361 A | 12/1997 | Evans et al. | |
| 5,795,331 A | 8/1998 | Cragg et al. | |
| 5,851,508 A | 12/1998 | Greff et al. | |
| 5,882,334 A | 3/1999 | Sepetka et al. | |
| 5,925,683 A | 7/1999 | Park | |
| 6,037,366 A | 3/2000 | Krall et al. | |
| 6,051,607 A | 4/2000 | Greff | |
| 6,096,848 A | 8/2000 | Gololobov et al. | |
| 6,143,352 A | 11/2000 | Clark et al. | |
| 6,160,025 A | 12/2000 | Slaikeu et al. | |
| 6,174,919 B1 | 1/2001 | Hickey | |
| 6,538,026 B1 * | 3/2003 | Krall et al. ................ | 514/527 |

FOREIGN PATENT DOCUMENTS

| | | |
|---|---|---|
| JP | 1197464 | 9/1989 |
| JP | 7033726 | 2/1995 |
| WO | WO 94/15907 | 7/1994 |
| WO | WO 96/39469 | 12/1996 |
| WO | WO 99/03404 | 1/1999 |
| WO | WO 00/44287 | 8/2000 |

OTHER PUBLICATIONS

Tseng et al., "Modified ethoxyethyl cyanoacrylate for therapeutic embolization of arteriovenous malformation," J. Bomed. Mater. Research. 24, 65-78 (1990).*
Biochemistry: The Chemical Reactions of Living Cells by David E. Metzler, p. 3.*
Handbook of chemistry and Physics, 57th edition, 1976-1977, p. F-112.*
Vinters et al., "The Histotoxicity of Cyanoacrylate: A Selective Review," Neuroradiology 27, 279-91 (1985).
Oowaki et al., "Non-adhesive cyanoacrylate as an embolic material for endovascular neurosurgery," Biomaterials 21(10), 1039-46 (2000).
Kennedy, J.P. et al., "Macromers by carbocationic polymerization. X. Synthesis, characterization, and polymerizability of cyanoacrylate-capped polyisobutylenes," J. Macromol. Sci-Chem. A28(2), 209-24 (1991).
Tseng et al., "Modified ethoxyethyl cyyanoacrylate for therapeutic emobolization of arteriovenous malformation," J. Biomed. Mater. Res. 24, 65-77 (1990).
Kerber et al., "Liquid acrylic adhesive agents in interventional neuroradiology," Neurosurg. Clin. N. Am. 11(1), 85-99, viii-ix (1990).
Higashida R.T. et al., "Intracranial aneurysms. Evolution and future role of endovascular techniques." Neurosurg. Clin. N. Am. 5(3), 413-25 (1994).
Tseng et al., "In vitro toxicity test of 2-cyanoacrylate polymers by cell culture method." J. Biomed. Mater. Res. 24, 1355-67 (1990).
Brothers et al., "n-Butyl 2-cyanoacrylate—substitute for IBCA in interventional neuroradiology: Histopathologic and polymerization time studies." Am. J. Neurorad. 10, 777-86 (1989).
Spiegel et al., "Adjusting the polymerization time of isobutyl-2-cyanoacrylate." Am. J. Neurorad. 7, 109-112 (1986).
Klemarczyk P., "Adhesion studies of mixtures of ethyl cyanoacrylate with a difunctional cyanoacrylate monomer and with other electron-deficient olefins." J. Adhesion 69, 293-306 (1999).
Buck, C.J., "Unequivocal synthesis of bis(2-cyanoacrylate) monomers. I. Via anthracene adducts." J. Polym. Sci.: Polym. Chem. Ed. 16, 2475-2507 (1978).

* cited by examiner

*Primary Examiner*—Michael G. Hartley
*Assistant Examiner*—Blessing Fubara
(74) *Attorney, Agent, or Firm*—Vista IP Law Group LLP

(57) ABSTRACT

The present invention provides an occlusive composition comprising: a) a poly(2-cyanoacrylate) monomer of the following formula (I):

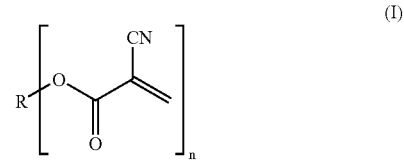

(I)

wherein n≧2 and R is an organic moiety; and b) a visualization agent. The present invention also provides a method for creating a solid mass in an ionic fluid-containing bodily cavity within a living organism, comprising delivering into the bodily cavity a clinically sufficient amount of an occlusive composition comprising a poly(2-cyanoacrylate) monomer of formula (I) and a visualization agent.

17 Claims, No Drawings

OCCLUSIVE COMPOSITION

BACKGROUND

1. Field of the Invention

The present invention is directed to a composition that can be used to create a solid mass in a bodily cavity within a living organism. More particularly, this invention relates to an occlusive composition comprising a monomer having two or more reactive cyanoacrylate sites, wherein the polymeric solid formed therefrom has reduced toxicity.

2. Background

The ability to create a solid mass in a bodily cavity can be beneficial in a variety of situations. For example, a solid occlusion can be used to block fallopian tubes for sterilization, to control bleeding from a wound or during surgery, or to cut off blood flow to a tumor, or to a diseased blood vessel, such as an arteriovenous malformation (AVM), an aneurysm, or an arteriovenous fistula.

There are a number of known methods for creating occlusions, each of which involves introducing a solid obstruction into a luminal cavity. Examples of solid obstructions include thin wire microcoils of platinum or stainless steel, and water-insoluble polymers.

A solid occlusion can be created from a water-insoluble polymer in a number of ways. For example, a preformed polymer can be dissolved in a suitable solvent, such as ethanol, and then injected directly into a luminal cavity. Upon contacting the aqueous fluid in the lumen (usually blood), the polymer precipitates from the solution and blocks the passageway. See, e.g., U.S. Pat. No. 6,160,025 (Slaikeu et al.). Alternatively, a reactive monomer can be introduced into the lumen. When the monomer contacts the aqueous, anion-containing fluid (e.g., blood), it polymerizes in situ, blocking the passageway. See, e.g., U.S. Pat. No. 5,695,480 (Evans et al.).

The reactive monomers most commonly used for in situ polymerization are alkyl-2-cyanoacrylates having one polymerizable cyanoacrylate group per monomer, such as n-butyl-2-cyanoacrylate. Upon contact with anions, these monomers react quickly to form linear polymers. The rapid rate of polymer growth causes a rapid increase in viscosity, which is necessary for localized formation of an occlusive mass.

However, the simple alkyl-2-cyanoacrylates have a number of drawbacks. For example, they generate an undesirable amount of heat as they rapidly polymerize. Also, the rapidly forming, adhesive polymers can trap the injection catheters, making it difficult to safely remove the instruments. Moreover, if an occluded lumen is to be resected, the occlusive polymer formed from a common alkyl-2-cyanoacrylate monomer is often too stiff or too brittle to be easily removed during resection. In addition, such polymers release the toxic chemical formaldehyde as they break down. Another drawback of the simple alkyl-2-cyanoacrylates is that the unreacted monomers themselves can cause toxic effects in surrounding tissues. See, e.g., Vinters et al., "The Histotoxicity of Cyanoacrylate: A Selective Review," *Neuroradiology* 27, 279-291 (1985).

A potential means of addressing these drawbacks is to increase the chain length of an alkyl-2-cyanoacrylate, which may decrease the rate of biodegradation, and thereby reduce toxicity. But increasing chain length also may slow the rate of polymerization. And while slowing the polymerization rate has the benefit of reducing both heat generation and the risk of catheter entrapment, it also reduces the rate of viscosity increase—which may undermine the usefulness of long chain alkyl-2-cyanoacrylates as occlusive agents. See, e.g., Oowaki et al., "Non-adhesive cyanoacrylate as an embolic material for endovascular neurosurgery," *Biomaterials* 21(10), 1039-46 (2000).

Consequently, the most common way that the prior art has addressed these and other problems associated with alkyl-2-cyanoacrylate monomers has been to combine various additives with the monomers, thereby increasing the complexity of the compositions. For example, U.S. Pat. No. 6,037,366 (Krall et al.) describes the use of a composition comprising six additives in two mixtures, which must be combined within four hours of use. Other prior art solutions are described in U.S. Pat. No. 5,624,669 (Leung et al.), where formaldehyde scavengers are used as additives, and WO 00/44287 (Krall et al.), where polymerization inhibitors are added to the embolic composition. By way of example, the typical formulation of an n-butyl cyanoacrylate embolic composition, such as TRUFILL-nBCA (Cordis Neurovascular, Inc., Miami Fla.), requires the physician to mix the monomer with an ethiodized oil additive as a polymerization inhibitor.

Thus, a need exists for an occlusive composition comprising a reactive monomer having the following properties: a) the reactive monomer polymerizes upon contact with an aqueous ionic environment, b) the viscosity of the polymerizing mass increases rapidly enough to create a highly localized occlusion in a high fluid flow environment, c) the polymerization rate is slow enough to minimize heat generation, d) the growing polymeric mass does not impede the removal of an injection catheter, e) the resulting polymeric mass has minimal toxicity, and f) the resulting mass is flexible enough to facilitate resection. A need especially exists for an occlusive composition having these attributes, wherein the composition does not contain a complex mixture of additives.

SUMMARY OF THE INVENTION

The present invention provides such a composition. More specifically, the present invention provides an occlusive composition comprising: a) a poly(2-cyanoacrylate) monomer of the following formula (I):

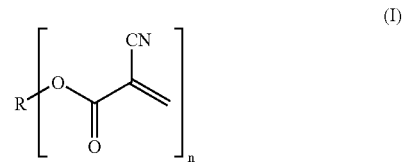

wherein $n \geq 2$ and R is an organic moiety; and b) a visualization agent.

The present invention also provides a method for creating a solid mass in an ionic fluid-containing bodily cavity within a living organism, comprising delivering into the bodily cavity a clinically sufficient amount of an occlusive composition comprising a poly(2-cyanoacrylate) monomer of formula (I) and a visualization agent.

DETAILED DESCRIPTION OF THE PREFERRED EMBODIMENTS

A monomer having multiple cyanoacrylate reactive sites per molecule—a poly(2-cyanoacrylate) monomer—can be synthesized according to known methods. Although a variety of protecting groups, activating groups, and/or intermediates are necessarily involved, the ultimate starting materials for the synthesis of a monomer having multiple cyanoacrylate reactive sites per molecule are 2-cyanoacrylic acid and a molecule having multiple hydroxyl groups per molecule—i.e., a polyol. The following Scheme 1 is a general depiction of a poly(2-cyanoacrylate) and its ultimate starting materials, in the form of a retrosynthetic analysis, where $n \geq 2$:

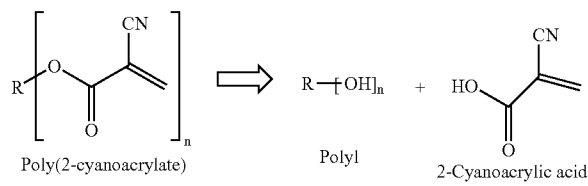

Poly(2-cyanoacrylate)      Polyl      2-Cyanoacrylic acid

For example, U.S. Pat. Nos. 5,504,252 (Klemarczyk), 6,096,848 (Gololobov et al.), 3,975,422 (Buck), and 3,142,698 (Halpern et al.), and Buck, C. J., "Unequivocal synthesis of bis(2-cyanoacrylate) monomers. I. Via anthracene adducts." J. Polym. Sci.: Polym. Chem. Ed. 16, 2475-2507 (1978) all describe syntheses of bis(2-cyanoacrylates) (n=2 in Scheme 1). The synthesis of poly(2-cyanoacrylates) having three or more cyanoacrylate reactive groups per molecule ($n \geq 3$) are described in WO 94/15907 (Dyatlov et al.), JP 01197464 (Kameyama et al.), and JP 7033726 (Asako et al.).

The present invention is directed to an occlusive composition comprising a poly(2-cyanoacrylate) monomer. "Occlusive composition" is defined as a composition that is suitable for creating a solid mass, such as an embolism, in a bodily cavity, such as a lumen. The occlusive composition and methods of this invention can be used in applications such as tissue bulking, localized delivery of bioactive agents, and sterilization via blockage of the fallopian tubes. Preferred uses of the occlusive composition and methods of this invention include the prevention of blood flow through a variety of vascular abnormalities, such as arteriovenous malformations (AVMs), arteriovenous fistulas, or aneurysms, and the prevention of blood flow through healthy blood vessels—to starve tumors, for example.

Ideally, the occlusive composition forms a solid mass rapidly upon introduction into a bodily cavity, forming the solid mass in the vicinity of the introduction site, so that only a safe quantity—preferably, substantially none—of the composition travels beyond the local area of introduction. At the same time, where a catheter is used to inject the occlusive composition into the bodily cavity, the rate of solid mass formation, and the adhesiveness of the polymer itself, is low enough so that the solid mass does not entrap the catheter.

More specifically, the invention relates to an occlusive composition comprising: a) a poly(2-cyanoacrylate) monomer of the following formula (I):

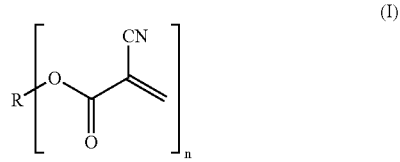

(I)

wherein $n \geq 2$ and R is an organic moiety, and b) a visualization agent. By "organic moiety" is meant any atom or group of atoms, provided that at least one such atom is a carbon atom. By varying the length and/or functionality of the organic moiety (the R group), the physical properties of the poly(2-cyanoacrylate) monomer can be altered, as can the properties of the resulting polymeric mass (e.g., monomer properties such as polymerization rate, melting point, solubility, radiopacity, viscosity, and rate of viscosity increase, and polymer properties such as flexibility/stiffness, radiopacity, and solubility). For example, lengthening the R group of the poly(2-cyanoacrylate) monomer will generally tend to increase monomer viscosity, decrease polymerization rate, and increase the flexibility of the polymer.

As shown in Scheme 1, the R group of the poly(2-cyanoacrylate) monomer is derived from the R group of the polyol starting material. Any polyol starting material that can be transformed into the poly(2-cyanoacrylate) monomer of Scheme 1 can thus furnish the R group in the monomer. Examples of such polyols include hydroxyl group containing polymers, such as hydroxyl group containing polyolefins, polysiloxanes, polyesters, polyethers, and polyurethanes. Consequently, the R group of the poly(2-cyanoacrylate) monomer can be a polymer, such as a polyolefin, polysiloxane, polyester, polyether, or polyurethane. For example, polyvinylalcohol, partially hydrolyzed polyvinylacetate, or bis(hydroxyl-terminated) poly(ethylene glycol), could be used to synthesize the poly(2-cyanoacrylate) monomer of the occlusive composition, and the R group would be the respective polyvinyl or poly(ethylene glycol) polymer. It should be noted that, as used herein, the term "polymer" includes oligomers comprising at least two monomer subunits.

Examples of preferred poly(2-cyanoacrylate) monomers having polymeric R groups are bis(2-cyanoacryl)polyisobutylene and tris(2-cyanoacryl)polyisobutylene. See Kennedy, J. P. et al., "Macromers by carbocationic polymerization. X. Synthesis, characterization, and polymerizability of cyanoacrylate-capped polyisobutylenes," J. Macromol. Sci-Chem. A28(2), 209-24 (1991). Generally preferred are bis (2-cyanoacrylates) derived from bis(hydroxyl-terminated) polymers of poly(ethylene glycol), poly(propylene glycol), poly(tetramethylene glycol), poly(isobutylene), poly(dimethyl siloxane), poly(glycolic acid), poly(lactic acid), polycaprolactone, other telechelic polymers, and copolymers thereof.

The R group of the poly(2-cyanoacrylate) monomer also can be derived from the PLURACOL® and POLY-G® families of polyethylene glycols and block copolymers such as the PLURONIC® family of poly(propylene glycol-block-ethylene glycol-block-propylene glycol) and poly(ethylene glycol-block-propylene glycol-block-ethylene glycol) copolymers (both available from BASF Corp., Mount Olive, N.J.). Additionally, the R group can be derived from star-shaped or dendritic polymers having terminal hydroxyl groups, such as multi-arm polyethylene glycols, which are commercially available from Shearwater Corp., Huntsville, Ala.

The R group of the poly(2-cyanoacrylate) monomer also can be derived from a polyhydroxy natural compound such as a sugar, starch, cellulose, cyclodextrin, or other carbohydrate. Additionally, generally suitable are R groups selected from the group consisting of straight chain or branched chain alkyl groups having 1 to 22 carbon atoms, straight chain or branched chain $C_{1-22}$ alkyl groups substituted with one or more functional groups, straight chain or branched chain alkenyl groups having 2 to 22 carbon atoms, straight chain or branched chain $C_{2-22}$ alkenyl groups substituted with one or more functional groups, straight chain or branched chain alkynyl groups having 2 to 22 carbon atoms, straight chain or branched chain $C_{2-22}$ alkynyl groups substituted with one or more functional groups, cycloaliphatic groups having 3 to 22 carbon atoms, $C_{3-22}$ cycloaliphatic groups substituted with one or more functional groups, aryl groups, aryl groups substituted with one or more functional groups, aralkyl groups, and aralkyl groups substituted with one or more functional groups, wherein said functional groups are each selected from the group consisting of halogen, ether, ester, amide, anhydride, carboxylic acid, aldehyde, ketone, hydroxyl, cyano, and isocyanato.

Further examples of the poly(2-cyanocrylate) monomer of the occlusive composition include ethylene glycol bis(2-cyanoacrylate), glycerol tris(2-cyanoacrylate), pentaerythritol tetrakis(2-cyanoacrylate), 1,3-propanediol bis(2-cyanoacrylate), 1,4-butanediol bis(2-cyanoacrylate), trans-2-butenediol bis(2-cyanoacrylate), 1,6-hexanediol bis(2-cyanoacrylate), 2,5-hexanediol bis(2-cyanoacrylate), 1,8-octanediol bis(2-cyanoacrylate), 1,9-nonanediol bis(2-cyanoacrylate), 1,10-decanediol bis(2-cyanoacrylate), 1,12-dodecanediol bis(2-cyanoacrylate), and 1,3-bis(hydroxymethyl) tetramethyldisiloxane bis(2-cyanoacrylate).

In addition to the poly(2-cyanoacrylate) monomer, the occlusive composition optionally may comprise a mono(2-cyanoacrylate) monomer of the following formula (II):

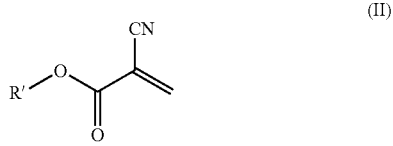

(II)

wherein R' is an organic moiety, as previously defined. In the same way as the R group of the poly(2-cyanoacrylate) monomer is derived, at least conceptually, from a polyol (Scheme 1), so the R' group of the mono(2-cyanoacrylate) monomer is derived from a mono- or polyol. The only difference is that when the R' group is derived from a polyol, only one hydroxyl group thereof is derivatized with a 2-cyanoacrylate group.

In other words, like the R group of the poly(2-cyanoacrylate) monomer, the R' group of the mono(2-cyanoacrylate) monomer can be derived from a hydroxyl group-containing polymer, such as a hydroxyl group containing polyolefin, polysiloxane, polyester, polyether, or polyurethane. The R' group also can be derived from a hydroxylated natural compound, such as a sugar, starch, cellulose, cyclodextrin, or other carbohydrate.

In addition, the R' group can be any group selected from the group consisting of straight chain or branched chain alkyl groups having 1 to 22 carbon atoms, straight chain or branched chain $C_{1-22}$ alkyl groups substituted with one or more functional groups, straight chain or branched chain alkenyl groups having 2 to 22 carbon atoms, straight chain or branched chain $C_{2-22}$ alkenyl groups substituted with one or more functional groups, straight chain or branched chain alkynyl groups having 2 to 22 carbon atoms, straight chain or branched chain $C_{2-22}$ alkynyl groups substituted with one or more functional groups, cycloaliphatic groups having 3 to 22 carbon atoms, $C_{3-22}$ cycloaliphatic groups substituted with one or more functional groups, aryl groups, aryl groups substituted with one or more functional groups, aralkyl groups, and aralkyl groups substituted with one or more functional groups, wherein said functional groups are each selected from the group consisting of halogen, ether, ester, amide, anhydride, carboxylic acid, aldehyde, ketone, hydroxyl, cyano, and isocyanato.

Specific examples of the mono(2-cyanoacrylate) monomer of formula (II) include ethyl-2-cyanoacrylate, propyl-2-cyanoacrylate, n-butyl-2-cyanoacrylate, isobutyl-2-cyanoacrylate, (2'-hexyl)-2-cyanoacrylate, n-hexyl-2-cyanoacrylate, n-octyl-2-cyanoacrylate, (2'-octyl)-2-cyanoacrylate, ethoxyethyl-2-cyanoacrylate, and isostearyl-2-cyanoacrylate. Preferred are n-butyl-2-cyanoacrylate, n-hexyl-2-cyanoacrylate, and n-octyl-2-cyanoacrylate.

Numerous techniques for the synthesis of mono(2-cyanoacrylates) are known in the art. See, e.g., U.S. Pat. Nos. 2,721,858, 3,254,111, 3,355,482, 3,654,340, 5,140,084, and 5,359,101 (Knoevenagel condensation), 3,463,804 and 4,012,402 (Diels-Alder protection/deprotection), and 5,504,252 (α-selenoxide elimination).

When the occlusive composition comprises the mono(2-cyanoacrylate) monomer of formula (II), the relative quantities of the monomers of formulas (I) and (II) in the occlusive composition is preferably such that the monomer of formula (II) comprises less than or equal to about 50% by weight of the total amount of the monomers of formulas (I) and (II) present in the occlusive composition. More preferably, the monomer of formula (II) comprises less than or equal to about 25% by weight of the total amount of the monomers of formulas (I) and (II) present in the occlusive composition. Still more preferably, the monomer of formula (II) comprises less than or equal to about 15% by weight of the total amount of the monomers of formulas (I) and (II) present in the occlusive composition. Even more preferably, the monomer of formula (II) comprises less than or equal to about 10% by weight of the total amount of the monomers of formulas (I) and (II) present in the occlusive composition. Most preferably, the monomer of formula (II) comprises less than or equal to about 5% by weight of the total amount of the monomers of formulas (I) and (II) present in the occlusive composition.

Although one or more monomers of formula (II) may be included in the occlusive composition, an advantage of the invention is that such a monomer is not necessary to overcome the problems associated with traditional occlusive compositions and techniques. As stated previously, occlusive compositions based on common mono(2-cyanoacrylates), such as n-butyl-2-cyanoacrylate, have the drawbacks of relatively high reaction rate, catheter adhesion, undesirable toxicity, and polymer stiffness. Prior art solutions to these and other problems associated with mono(2-cyanoacrylates) have involved combining a variety of additives with the monofunctional monomers. For example, U.S. Pat. No. 6,037,366 (Krall et al.) describes a seven component composition; the composition in U.S. Pat. No. 5,624,669 (Leung et al.) incorporates formaldehyde scavengers as additives; and the WO 00/44287 (Krall et al.) composition includes polymerization inhibitors.

In contrast, the occlusive composition of the present invention permits the same drawbacks to be overcome through the use of a single component—the poly(2-cyanoacrylate) of formula (I). Without wishing to be confined to any particular theory, it is believed that the advantages of the poly(2-cyanoacrylate) monomer derive at least in part from its ability to form cross-linked polymeric masses. As a result, even a relatively slow polymerization rate can provide a rapid increase in viscosity, which is necessary to form an occlusion in a high fluid flow environment.

In other words, longer chain poly(2-cyanoacrylate) monomers, which form more stable, less toxic, polymeric masses, still provide high rates of viscosity increase. Consequently, the most advantageous results are obtained when the molecular weight of the poly(2-cyanoacrylate) monomer is relatively high compared to that of the traditional alkyl-2-cyanoacrylate monomers, such as n-butyl-2-cyanoacrylate. It is preferred, for example, that the R group of the poly(2-cyanoacrylate) monomer of formula (I) has a molecular weight of at least about 200. More preferably, the R group of the poly(2-cyanoacrylate) has a molecular weight of at least about 400. And most preferably, the R group of the poly(2-cyanoacrylate) has a molecular weight of at least about 600.

The occlusive composition also contains a visualization agent. The visualization agent is any agent that renders the polymeric mass visible by means of a diagnostic imaging technique, such as fluoroscopy, radiography, or MRI. See, e.g., U.S. Pat. No. 5,695,480 (Evans et al.).

For example, the polymeric mass can be visualized by using a visualization agent that is radiopaque and localizes at the site of the mass, e.g., by being trapped within the rapidly forming polymeric mass. Suitable visualization agents include iodinated and brominated organic molecules, such as tetrafluorodibromoethane and hexafluorodibromopropane (see Tseng et al., "Modified ethoxyethyl cyanoacrylate for therapeutic embolization of arteriovenous malformation," *J. Biomed. Mater. Res.* 24, 65-77. (1990)), metrizamide (see U.S. Pat. No. 3,701,771 (Almen et al.)), iopromide, iopamidol, iohexol, iomeprol, ioversol, ioxilan, iodixanol, iotrolan, and other polyhydroxylated triiodinated isophthalic acid diamides (see U.S. Pat. No. 4,364,921 (Speck et al.)), iodized oils, such as iodinated poppyseed oil, and iodinated acids. Suitable iodinated acids include α-phenyl-β-(3,5-diiodo-4-hydroxyphenyl) propionic acid, 3-acetylaminomethyl-5-acetylamino-2,4,6-3-iodobenzoic acid, and α-(3-amino-2,4,6,-3-iodobenzyl) butyric acid (see U.S. Pat. No. 4,847,065 (Akimova et al.)). Suitable visualization agents also include commercially available compositions such as AMIPAQUE® and ULTRAVIST® (Winthrop-Breon Laboratories, a division of Sterling Drug, Inc.), PANTOPAQUE® and LIPIODOL® (Laboratories Guerbet, Aulnay-sous-Bois, France), and ETHIODOL® (Savage Laboratories, Melville, Md., U.S.A.). Powdered agents that are insoluble in blood, such as gold, platinum, tantalum, tantalum oxide, titanium, zirconium, zirconium oxide, tungsten, bismuth subcarbonate, and barium sulfate are also suitable. Preferably, the powdered agent has a particle size that is small enough to permit formation of a suspension that does not settle out within the time required for the occlusive composition to be delivered. On the other hand, the powdered agent preferably does not have a particle size so small that it forms a highly thixotropic mixture, which is difficult to inject through a microcatheter. Preferred are hydrophobic visualization agents such as ethiodized oil, LIPIODOL®, tetrafluorodibromoethane, and hexafluorodibromopropane, and/or powdered agents such as tantalum, tungsten, gold or platinum.

The visualization agent also can be one or more radiopaque functional groups, such as iodide and/or bromide, covalently incorporated as part of the R group of the poly(2-cyanoacrylate) monomer of formula (I) and/or covalently incorporated as part of the R' group of the mono(2-cyanoacrylate) monomer of formula (II). In either case, the occlusive composition would be simplified still further, since a single molecule would serve as both visualization agent and reactive monomer. Significantly, when the visualization agent is a functional group covalently incorporated as part of the R group of the poly(2-cyanoacrylate) monomer, a single-component occlusive composition is made possible.

By way of illustration, the R group of the poly(2-cyanoacrylate) monomer of formula (I) could be derived from a bromide and/or iodide-containing molecule having multiple hydroxyl groups, such as metrizamide, iopromide, iopamidol, iohexol, iomeprol, ioversol, ioxilan, iodixanol, iotrolan, or another polyhydroxylated triiodinated isophthalic acid diamide (see U.S. Pat. No. 4,364,921 (Speck et al.)). In the same way, the R' group of the mono(2-cyanoacrylate) monomer could be derived from a mono- or polyhydroxy bromide and/or iodide-containing molecule. When the R' group is derived from a polyhydroxy molecule, only one of the multiple hydroxyl groups is derivatized with a 2-cyanoacrylate group to form the mono(2-cyanoacrylate) monomer of formula (II).

When the visualization agent is a separate molecule (i.e., not covalently incorporated as part of the monomer of formula (I) and/or (II)), the visualization agent preferably comprises between about 10% and about 90% by weight of the occlusive composition. More preferably, the visualization agent comprises between about 15% and about 75% of the occlusive composition by weight. Still more preferably, the visualization agent comprises between about 20% and about 60% of the occlusive composition by weight. Most preferably, the visualization agent comprises between about 25% and about 50% of the occlusive composition by weight.

When the visualization agent is a functional group covalently incorporated as part of the R group of the poly(2-cyanoacrylate) monomer, the visualization agent preferably comprises at least about 15% of the R group by mass. More preferably, the visualization agent comprises at least about 25% of the R group by mass. Still more preferably, the visualization agent comprises at least about 35% of the R group by mass. Most preferably, the visualization agent comprises at least about 45% of the R group by mass.

In the same way, when the visualization agent is a functional group covalently incorporated as part of the R' group of the mono(2-cyanoacrylate) monomer, the visualization agent preferably comprises at least about 15% of the R' group by mass. More preferably, the visualization agent comprises at least about 25% of the R' group by mass. Still more preferably, the visualization agent comprises at least about 35% of the R' group by mass. Most preferably, the visualization agent comprises at least about 45% of the R' group by mass.

The occlusive composition optionally may comprise one or more additives that are soluble in, or miscible with, the other components of the occlusive composition, or that form stable emulsions or suspensions in the occlusive composition. The additives include, e.g., formaldehyde scavengers, polymerization inhibitors, plasticizers, rheology-modifying agents, liquid carriers, and bioactive agents.

For a description of suitable formaldehyde scavengers, see U.S. Pat. No. 5,624,669 (Leung et al.).

Suitable polymerization inhibitors include monomer stabilizers, such as hydroquinone, p-methoxyphenol, and phosphoric acid. See, e.g., WO 00/44287 (Krall et al.).

Suitable plasticizers impart properties such as flexibility, elasticity, and reduced catheter adhesion to the solid polymeric mass. Moreover, hydrophobic additives such as plasticizers may decrease the rate of formaldehyde release via polymer hydrolysis, and therefore reduce chronic toxicity, by limiting the amount of water uptake into the solid mass.

Suitable plasticizers include organic esters and low molecular weight polymers, preferably having glass transition temperatures below 20° C. Examples include aromatic esters, alkyl esters, phthalate esters, citrate esters, glycerol esters, plant-derived oils, animal derived oils, silicone oils, iodinated oils, and vitamins A and E, and acetates and esters thereof.

Suitable carriers include liquid polymers such as poly (ethylene glycol), poly(propylene glycol), poly(dimethylsiloxane), and solvents such as n-methyl pyrrolidone, dimethylsulfoxide (DMSO), ethanol, water, and other solvents used in pharmaceutical preparations.

When the occlusive composition includes one or more plasticizers and/or carriers, the plasticizers and/or carriers preferably comprise less than or equal to about 80% of the occlusive composition by weight. More preferably, the plasticizers and/or carriers comprise less than or equal to about 50% of the occlusive composition by weight. Still more preferably, the plasticizers and/or carriers comprise less than or equal to about 25% of the occlusive composition by weight. Most preferably, the plasticizers and/or carriers comprise less than or equal to about 10% of the occlusive composition by weight.

Rheology modifying agents can be used to alter the viscosity, cohesiveness, powder suspending ability, and radiopacity of the occlusive composition. Suitable rheology modifying agents include polymers, and fine, inorganic particulate materials. Examples of polymers that are suitable for use as rheology modifying agents include poly(acrylates), poly(olefins), poly(alkyl oxides), poly(amides), poly (carbonates), cellulosic polymers and copolymers, poly (dienes), poly(esters), poly(methacrylates), poly (saccharides), poly(siloxanes), poly(styrenes), poly (urethanes), poly(vinyl ethers), poly(vinyl esters), polymers and copolymers having a high iodine content, and other rubbery polymers compatible with the poly(2-cyanoacrylate) of formula (I). Examples of inorganic particulate materials that are suitable for use as rheology modifying agents include fumed silica, silicatious earth (e.g., bentonite), and other inorganic particulate gelling or suspending materials capable of altering the rheology of the occlusive composition to possess properties of a thixotropic, pseudo-plastic, or plastic fluid.

When the occlusive composition includes one or more rheology modifying agents, the rheology modifying agents preferably comprise less than or equal to about 20% by weight of the total mass of the occlusive composition. More preferably, the rheology modifying agents comprise less than or equal to about 10% by weight of the occlusive composition. Still more preferably, the rheology modifying agents comprise less than or equal to about 5% by weight of the occlusive composition. Most preferably, the rheology modifying agents comprise less than or equal to about 2% by weight of the occlusive composition.

Suitable bioactive agents include drugs, angiogenesis inhibiting agents, thrombogenic agents, anti-thrombogenic agents, chemotactic agents, inflammatory agents, anti-inflammatory agents, anesthetic agents, cell proliferation promoters and inhibitors, proteins, peptides, growth factors, cytokines, viral vectors, oligo- and polynucleotides, trace metals, disrupters of endothelial cells, cell fragments, spore-like cells, living cells, and agents containing the functional fragments of any of the above. When included in the occlusive composition, the bioactive agent or agents should be included in clinically sufficient amounts. That is, the bioactive agent or agents should be included in amounts sufficient to elicit the desired therapeutic response, such as angiogenesis inhibition, inflammation, inhibition of cell proliferation, etc. Methods of determining clinically sufficient amounts of bioactive agents to be delivered into bodily cavities are well known to those of skill in the art.

Examples of angiogenesis inhibiting agents include extracts from cartilage tissue showing collagenase-inhibiting activity, angiostatic steroid protein, obtained from retinal pigment epithelial cells, anti-cancer factor induced from cultured cartilage cells, ribonuclease inhibitors, herbimycin A, fumagillin produced by microorganisms, and fumagillol derivatives chemically synthesized. See, e.g., U.S. Pat. No. 5,202,352 (Okada et al.)

Examples of suitable thrombogenic agents include collagen, fibrinogen, and vitronectin. Suitable growth factors include vascular endothelial growth factor (VEGF), acidic and basic fibroblast growth factors, epidermal growth factor, transforming growth factor $\alpha$ and $\beta$, platelet-derived endothelial growth factor, platelet-derived growth factor, tumor necrosis factor $\alpha$, hepatocyte growth factor, and insulin like growth factor. Examples of suitable anesthetic agents include lidocaine, bupivacaine, and ropivacaine. Examples of therapeutic polynucleotides include anti-sense DNA and RNA, DNA coding for an anti-sense RNA, and DNA coding for tRNA or rRNA to replace defective or deficient endogenous molecules, or for the synthesis of bioactive protein agents. Cell proliferation inhibitors, including agents for treating malignancies, include CDK inhibitors and thymidine kinase. Examples of suitable proteins and peptides include the families of cytokines, growth factors, enzymes, coagulation proteins, plasma proteins, extracellular matrix proteins, and their functional peptides.

The invention also provides a method for creating a solid mass in an ionic fluid-containing bodily cavity within a living organism, comprising delivering into the bodily cavity a clinically sufficient amount of the previously described occlusive composition. By a "clinically sufficient amount" is meant a quantity sufficient to cause a solid mass to be formed within the bodily cavity. When the bodily cavity is a lumen, such as a blood vessel, the amount should be sufficient so that the solid mass blocks the flow of fluid through the lumen. When the bodily cavity comprises tissue to be bulked, the amount should be sufficient so that the solid mass bulks (i.e., strengthens or increases the effective volume of) the tissue. The quantity of the occlusive composition necessary to create a sufficient solid mass will vary in any given case depending on known parameters, such as the volume of the bodily cavity to be filled, the concentration of the poly(2-cyanoacrylate) monomer in the composition, and the rate of viscosity increase of the polymerizing monomers.

By "ionic fluid" is meant any fluid that contains charged molecules (especially anions) capable of catalyzing the polymerization of the poly(2-cyanoacrylate) monomer. Preferred examples of ionic fluids are blood, lymph, and extra-cellular fluid.

The occlusive composition used in the inventive method may optionally comprise any or all of the components previously described. For example, the occlusive composition may optionally comprise one or more bioactive agents. The invention thus provides a method for the therapeutic treatment of a living organism, comprising delivering to a bodily cavity a clinically sufficient amount of the occlusive composition comprising one or more bioactive agents.

Any suitable means may be used to deliver the occlusive composition into the bodily cavity, e.g., by injection through a needle or catheter, or via stereotaxic placement device. Common means of delivery are by way of a catheter or microcatheter, such as the TRACKER® EXCEL™, EXCELSIOR™, RENEGADE™, and SPINNAKER ELITE™ microcatheters (all from Target Therapeutics, Inc., Fremont, Calif.). Typically, the occlusive composition is delivered via a catheter device that has been rinsed free of ionic species, e.g., by prefilling the catheter device with a nonionic solution such as an aqueous 5% dextrose solution.

The inventive method is particularly suitable for tissue bulking and for creating embolisms in blood vessels, for example, to treat aneurysms, arteriovenous malformations, fistulas, or the feeding arteries of tumors. Common procedures for delivering occlusive compositions into blood vessels are described in, e.g., U.S. Pat. Nos. 5,624,669 (Leung et al.), 5,702,361 (Evans et al.), 5,882,334 (Sepetka et al.), and 5,925,683 (Park), WO 00/44287 (Krall et al.), Kerber, C. W. and Wong, W., "Liquid acrylic adhesive agents in interventional neuroradiology," *Neurosurg. Clin. N. Am.* 11(1), 85-99, viii-ix (1990), and Higashida R. T., Halbach V. V., Dowd C. F., Hieshima G. B., "Intracranial aneurysms. Evolution and future role of endovascular techniques." *Neurosurg. Clin. N. Am.* 5(3), 413-25 (1994).

The occlusive composition can be administered alone or in combination with another endoluminal device, which acts to confine the occlusive composition within a lumen. The latter combination technique may be especially useful when the endoluminal device is an endovascular device—for example, in the treatment of aneurysms. Examples of suitable endovascular devices include balloon catheters, stents, stent-grafts, and other endovascular devices capable of causing a temporary or permanent obstruction to movement of the occlusive composition outside of the vascular or aneurysmal cavity. Preferred endovascular devices include the SENTRY™ balloon catheter and the TRISPAN™ coil (both from Boston Scientific/TARGET; Fremont, Calif.), and the devices disclosed in WO 99/03404 and U.S. Pat. No. 5,795,331.

All patents, patent applications, and publications cited herein are incorporated by reference in their entirety to the same extent as if each individual reference was specifically and individually indicated to be incorporated herein by reference in its entirety.

While various embodiments, aspects, and applications of this invention have been described, it will be apparent to those skilled in the art that many more modifications are possible without departing from the inventive concepts herein. These modifications and variations are intended to be within the scope of the claims that follow.

EXAMPLE

Preparation of poly(2-cyanoacrylate) Derivative of iopamidol

To a 1000 ml 3-neck flask equipped with a Dean-Stark trap, condenser, thermometer, and nitrogen inlet, is added methyl-2-cyanoacrylate (45 g, 413 mmol), iopamidol (50 g, 64 mmol), dry toluene (500 ml), and an effective, catalytic amount of a solid, acidic ion-exchange resin [e.g., 2.5 g (ca. 5 mmol) of Dowex® Monosphere DR-2030 (Dow Chemical Co., Midland Mich.) (preferably washed free of residual moisture with an anhydrous alcohol, such as ethanol)] under nitrogen. The solution is heated to reflux with stirring. Solvent is removed through the Dean-Stark trap and replaced with an equal volume of fresh dry toluene. After refluxing for 8 hours, the solution is cooled to room temperature. The ion exchange resin is removed via filtration, and the reaction mixture is concentrated under vacuum. The reaction provides, as a mixture, iopamidol derivatized with up to five 2-cyanocrylate groups. For storage purposes, the mixture is preferably stabilized with an effective amount (e.g., ca. 5 mg) of a polymerization inhibitor such as hydroquinone, p-methoxyphenol, pure phosphoric acid and/or sulfur dioxide.

What is claimed is:

1. An occlusive composition comprising: a) a poly(2-cyanoacrylate) monomer of the following formula (I):

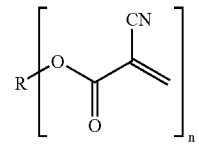

wherein n≧2 and R is an organic moiety, and b) a visualization agent.

2. The occlusive composition of claim 1, further comprising a mono(2-cyanoacrylate) monomer of the following formula (II):

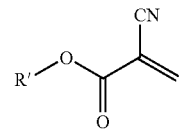

wherein R' is an organic moiety.

3. The occlusive composition of claim 1, wherein n=2.

4. The occlusive composition of claim 1, wherein n≧3.

5. The occlusive composition of claim 3, wherein R is derived from a bis(hydroxylterminated) polymer, the polymer being selected from the group consisting of poly(ethylene glycol), poly(propylene glycol), poly(tetramethylene glycol), poly(isobutylene), poly(dimethyl siloxane), poly(propylene glycol-block-ethylene glycol-block-propylene glycol), poly(glycolic acid), poly(lactic acid), polycaprolactone, and copolymers thereof.

6. The occlusive composition of claim 2, wherein the monomer of formula (II) comprises less than or equal to about 50% by weight of the total amount of the monomers of formulas (I) and (II) present in the occlusive composition.

7. The occlusive composition of claim 1, wherein R has a molecular weight of at least about 200 g/mol.

8. The occlusive composition of claim 7, wherein R has a molecular weight of at least about 400 g/mol.

9. The occlusive composition of claim 8, wherein R has a molecular weight of at least about 600 g/mol.

10. The occlusive composition of claim 1, wherein the visualization agent is one or more radiopaque functional groups covalently incorporated as part of the R group.

11. The occlusive composition of claim 1, further comprising one or more additives selected from the group consisting of formaldehyde scavengers, polymerization inhibitors, plasticizers, rheology-modifying agents, liquid carriers, and bioactive agents.

12. The occlusive composition of claim 11, wherein said one or more additives are selected from the group consisting of plasticizers and liquid carriers.

13. A method for creating a solid mass in an ionic fluid-containing bodily cavity within a living organism, comprising delivering into the bodily cavity a clinically sufficient amount of the occlusive composition of claim 1.

14. The method of claim 13, wherein the bodily cavity comprises at least one blood vessel, and the ionic fluid is blood.

15. The method of claim 13, wherein the bodily cavity is an aneurysm, an arteriovenous malformation, a fistula, or the feeding artery of a tumor.

16. A method for tissue bulking in a living organism, comprising delivering into a tissue a clinically sufficient amount of the occlusive composition of claim 1.

17. A method for the therapeutic treatment of a living organism, comprising delivering to a bodily cavity a clinically sufficient amount of the occlusive composition of claim 1, wherein said composition further comprises a clinically sufficient amount of one or more bioactive agents.

* * * * *